US 6,593,343 B2

(12) United States Patent
Björk et al.

(10) Patent No.: US 6,593,343 B2
(45) Date of Patent: *Jul. 15, 2003

(54) QUINOLINE DERIVATIVES

(75) Inventors: Anders Björk, Bjärred (SE); Stig Jönsson, Lund (SE); Tomas Fex, Lund (SE); Gunnar Hedlund, Lund (SE)

(73) Assignee: Active Biotech AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/131,176

(22) Filed: Apr. 25, 2002

(65) Prior Publication Data

US 2002/0173519 A1 Nov. 21, 2002

Related U.S. Application Data

(63) Continuation of application No. 09/618,060, filed on Jul. 17, 2000, now abandoned, which is a continuation of application No. 09/352,886, filed on Jul. 14, 1999, now Pat. No. 6,133,285.
(60) Provisional application No. 60/092,967, filed on Jul. 15, 1998, now abandoned.

(51) Int. Cl.$^7$ .................. A61K 31/4704; C07D 215/56; A61P 29/00; A61P 37/00
(52) U.S. Cl. .................... 514/312; 514/232.8; 514/291; 544/128; 546/90; 546/155
(58) Field of Search ............................. 514/312, 232.8, 514/291; 546/155, 90; 544/128

(56) References Cited

U.S. PATENT DOCUMENTS

| 4,547,511 A | * 10/1985 | Eriksoo et al. ........ 514/252.04 |
| 4,738,971 A | * 4/1988 | Eriksoo et al. ............. 514/291 |
| 5,580,882 A | * 12/1996 | Abramsky et al. .......... 514/312 |
| 5,594,005 A | * 1/1997 | Slavin et al. ............... 514/311 |
| 5,726,183 A | 3/1998 | Nilsson |
| 5,728,713 A | 3/1998 | Nilsson |
| 6,077,851 A | * 6/2000 | Bjork et al. ................. 514/312 |
| 6,133,285 A | * 10/2000 | Bjork et al. ............ 514/232.8 |

FOREIGN PATENT DOCUMENTS

| EP | 0 059 698 | 9/1982 |
| GB | 2 290 786 | 1/1996 |
| WO | WO 92-18483 | 10/1992 |
| WO | WO 95-24195 | 9/1995 |
| WO | WO 95-24196 | 9/1995 |
| WO | WO 95-24395 | 9/1995 |

OTHER PUBLICATIONS

Andersen et al, "Linomide reduced the rate of active lesions in relapsing–remitting multiple sclerosis", *Neurology* 47:895–900 (1996).
Bai et al, "Linomide–induced suppression of experimental autoimmune neuritis is associated with down–regulated macrophage function", *J. Neuroimmunol.* 76:177–184 (1997).
Gonzalo et al, "Linomide, a novel immunomodulator that prevents death in four models of septic shock", *Eur. J. Immunol.* 23:2372–2374 (1993).
Gonzalo et al, "Linomide inhibits programmed cell death of peripheral T cells in vivo", *Eur. J. Immunol.* 24:48–52 (1994).
Gross et al, "Prevention of diabetes mellitus in non–obese diabetic mice by linomide, a novel immunolmodulating drug", *Diabetologia* 37:1195–1201 (1994).
Harcourt, "Polyarteritis in colony of beagles", *The Veterinary Records*, 102:519–522 (1978).
Kalland, "Regulation of Natural Killer Progenitors", *J. Immunol.* 144:4472–4476 (1990).
Karussis et al, "Treatment of chronic–relapsing experimental autoimmune encephalomyelitis with the synthetic immunomodulator linomide (quinoline–3–carboxamide)", *Proc. Natl. Acad. Sci.* 90:6400–6404 (1993).
Karussis et al, "Immunomodulation of experimental autoimmune myasthenia gravis with linomide", *J. Neuroimmunol.* 55:187–193 (1994).
Karussis et al, Treatment of secondary progressive multiple sclerosis with the immunomodulator linomide, *Neurology* 47:341–346 (1996).
Larrson, "Mechanism of Action in the New Immunomodulator LS2616 on T cells Response", *Int. J. Immunol.* 9(4):426–431 (1987).
Prineas, "The neuropathology of multiple sclerosis", *Handbook of Clinical Neurology* 3(47):213–257 (1985).
Talal, "Autoimmune Disease", *Autoimmune Disease* pp. 195–198.
Tarkowski et al, "Successful Treatment of Autoimmunity in MRL/1 Mice with LS–2616, a new immunomodulator", *Arthritis and Rheumatism* 29(11):1405–1409 (1986).
Wanders et al, "Abolition of the Effects of Cyclosporine on Rat Cardiac Allograft Rejection by the New Immunomodulator LS–2616 (Linomide)", *Transplantation* 47:216–217 (1989).
Abstract: Japanese patent No. 07224040; Aug. 8, 1995.
Abstract: Japanese patent No. 07252228; Oct. 3, 1995.

* cited by examiner

Primary Examiner—Evelyn Mei Huang
(74) Attorney, Agent, or Firm—Browdy and Neimark

(57) ABSTRACT

Compounds of formula (I)

(I)

[Chemical structure of quinoline derivative with substituents $R_5$, $OR_4$, $R_6$, R', R'', R, and $CH_3$]

and tautomers thereof are effective for the treatment of mammals suffering from diseases resulting from autoimmunity and pathological inflammation.

15 Claims, No Drawings

QUINOLINE DERIVATIVES

CROSS REFERENCE TO RELATED APPLICATIONS

This is a continuing application from parent application Ser. No. 09/618,060, filed Jul. 17, 2000 abandoned, itself a continuing application from U.S. application Ser. No. 09/352,886 filed Jul. 14, 1999, now U.S. Pat. No. 6,133,285, which claims benefit of U.S. provisional application No. 60/092,967, filed Jul. 15, 1998, now abandoned, the contents of all of which are incorporated by reference.

FIELD OF THE INVENTION

The present invention relates to novel substituted quinoline-3-carboxamide derivatives, to methods for their preparation, to compositions containing them, and to methods and use for clinical treatment of disease resulting from autoimmunity, such as multiple sclerosis, insulin-dependent diabetes mellitus, systemic lupus erythematosus, rheumatoid arthritis, inflammatory bowel disease and psoriasis and, furthermore, diseases where pathologic inflammation plays a major role, such as asthma, atherosclerosis, stroke and Alzheimer's disease. More particularly, the present invention relates to novel quinoline derivatives suitable for the treatment of, for example, multiple sclerosis and its manifestations.

BACKGROUND OF THE INVENTION

Autoimmune diseases, e.g. multiple sclerosis (MS), insulin-dependent diabetes mellitus (IDDM), systemic lupus erythematosus (SLE), rheumatoid arthritis ($R_A$), inflammatory bowel disease (IBD) and psoriasis represent assaults by the body's immune system which may be systemic in nature, or else directed at individual organs in the body. They appear to be diseases in which the immune system makes mistakes and, instead of mediating protective functions, becomes the aggressor (1).

MS is the most common acquired neurologic disease of young adults in Western Europe and North America. It accounts for more disability and financial loss, both in lost income and in medical care, than any other neurologic disease of this age group. There are approximately 250.000 cases of MS in the United States.

Although the cause of MS is unknown, advances in brain imaging, immunology, and molecular biology have increased researchers' understanding of this disease. Several therapies are currently being used to treat MS, but no single treatment has demonstrated dramatic treatment efficacy. Current treatment of MS falls into three categories: treatment of acute exacerbations, modulation of progressive disease, and therapy for specific symptoms.

MS affects the central nervous system and involves a demyelination process, i.e., the myelin sheaths are lost whereas the axons are preserved. Myelin provides the isolating material that enables rapid nerve impulse conduction. Evidently, in demyelination, this property is lost. Although the pathogenic mechanisms responsible for MS are not understood, several lines of evidence indicate that demyelination has an immunopathologic basis. The pathologic lesions, the plaques, are characterized by infiltration of immunologically active cells such as macrophages and activated T cells (2).

In U.S. Pat. No. 4,547,511 and in U.S. Pat. No. 4,738,971 and in EP 59,698 some derivatives of N-aryl-1,2-dihydro-4-substituted-1-alkyl-2-oxo-quinoline-3-carboxamide are claimed as enhancers of cell-mediated immunity. The compound

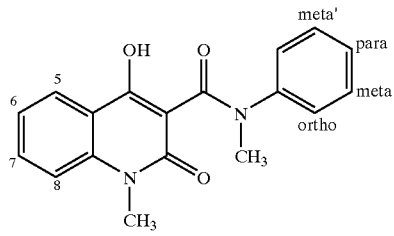

Roquinimex known as roquinimex (Merck Index 12$^{th}$ Ed., No. 8418; Linomide®, LS2616, N-phenyl-N-methyl-1,2-dihydro-4-hydroxy-1-methyl-2-oxo-quinoline-3-carboxamide) belongs to this series of compounds. Roquinimex has been reported to have multiple immunomodulatory activities not accompanied with general immunosuppression (3–12).

Furthermore, in U.S. Pat. No. 5,580,882 quinoline-3-carboxamide derivatives are claimed to be useful in the treatment of conditions associated with MS. The particular preferred compound is roquinimex. In U.S. Pat. No. 5,594,005 quinoline-3-carboxamide derivatives are claimed to be useful in the treatment of type I diabetes. The particular preferred compound is roquinimex.

In WO 95/24195 quinoline-3-carboxamide derivatives are claimed to be useful in the treatment of inflammatory bowel disease. Particularly preferred compounds are roquinimex or a salt thereof. In WO95/24196 quinoline-3-carboxamide derivatives are claimed to be useful in the treatment of psoriasis. Particularly preferred compounds are roquinimex or a salt thereof.

In clinical trials comparing roquinimex to placebo, roquinimex was reported to hold promise in the treatment of conditions associated with MS (13,14). There are, however, some serious drawbacks connected to roquinimex. For example, it has been found to be teratogenic in the rat, and to induce dose-limiting side effects in man, e.g. a flu-like syndrome, which prevents from using the full clinical potential of the compound.

Further, in WO 92/18483 quinoline derivatives substituted in the 6-position with a $RAS(O)_n$-group ($R_A$=lower alkyl or aryl; n=0-2) are claimed, which posses an immunomodulating, anti-inflammatory and anti-cancer effect.

The substitution, i.e., type and pattern, of the above, specifically mentioned, compounds in the prior art places them outside the scope of the present invention.

DESCRIPTION OF THE INVENTION

A primary objective of the present invention is to provide structurally novel quinoline compounds which by virtue of their pharmacological profile, with high potency in experimental models and low level of side-effects, are considered to be of value in the treatment of disease resulting from autoimmunity and pathologic inflammation. Examples of such disease are multiple sclerosis, insulin-dependent diabetes mellitus, systemic lupus erythematosus, rheumatoid arthritis, inflammatory bowel disease and psoriasis and other diseases where inflammation plays a major role, such as asthma, atherosclerosis, stroke and Alzheimer's disease. More particularly, the present invention relates to novel quinoline derivatives suitable for the treatment of, for example, multiple sclerosis and its manifestations.

The term "treatment" as used herein includes prophylaxis as well as relieving the symptoms of disease.

It has now surprisingly been found that the novel compounds of general formula (I)

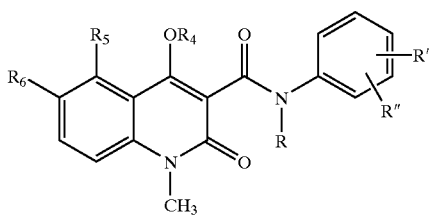

(I)

wherein

R is selected from methyl, ethyl, n-propyl, iso-propyl, n-butyl and allyl;

R' is selected from methyl, methoxy, fluoro, chloro, bromo, trifluoromethyl, and $OCH_xF_y$,
wherein x=0-2,
y=1-3 with the proviso that
x+y=3;

R" is selected from hydrogen, fluoro and chloro, with the proviso that R" is selected from fluoro and chloro only when R' is selected from fluoro and chloro;

$R_4$ is selected from hydrogen and pharmaceutically acceptable inorganic cations, such as sodium, potassium and calcium, and organic cations such as monoethanolamine, diethanolamine, dimethylaminoethanol, morpholine and the like;

$R_5$ is selected from ethyl, n-propyl, iso-propyl, methoxy, ethoxy, chloro, bromo, trifluoromethyl, and $OCH_xF_y$, and $OCH_2CH_xF_y$
wherein x=0-2,
y=1-3 with the proviso that
x+y=3;

$R_6$ is hydrogen; or $R_5$ and $R_6$ taken together are methylenedioxy;

are unexpectedly effective and specific in the treatment of individuals suffering from autoimmune and inflammatory diseases.

The compounds of general formula (I) may exist in different tautomeric forms and all such forms where such forms exist are included herein.

In a preferred embodiment of the invention $R_4$ is selected from hydrogen or sodium, $R_5$ is selected from ethyl, methoxy, chloro and trifluoromethyl, $R_5$ and $R_6$ taken together are methylenedioxy, R' is selected from methyl, methoxy, fluoro, chloro and trifluoromethyl when R" is hydrogen and R" is selected from metal- and para-fluoro provided that R' is ortho-fluoro.

Among the most preferred compounds of general formula (I) according to the present invention are:

N-ethyl-N-(3-fluoro-phenyl)-1,2-dihydro-4-hydroxy-5-chloro-1-methyl-2-oxo-quinoline-3-carboxamide, N-ethyl-N-(4-methoxy-phenyl)-1,2-dihydro-4-hydroxy-5-chloro-1-methyl-2-oxo-quinoline-3-carboxamide, N-methyl-N-(2,4-difluoro-phenyl)-1,2-dihydro-4-hydroxy-5-chloro-1-methyl-2-oxo-quinoline-3-carboxamide, N-methyl-N-(2,5-difluoro-phenyl)-1,2-dihydro-4-hydroxy-5-chloro-1-methyl-2-oxo-quinoline-3-carboxamide, N-ethyl-N-(3-methoxy-phenyl)-1,2-dihydro-4-hydroxy-5-ethyl-1-methyl-2-oxo-quinoline-3-carboxamide, N-methyl-N-(2-fluoro-phenyl)-1,2-dihydro-4-hydroxy-5-methoxy-1-methyl-2-oxo-quinoline-3-carboxamide, N-methyl-N-(2,4-difluoro-phenyl)-1,2-dihydro-4-hydroxy-5-methoxy-1-methyl-2-oxo-quinoline-3-carboxamide, N-methyl-N-(2,5-difluoro-phenyl)-1,2-dihydro-4-hydroxy-5-methoxy-1-methyl-2-oxo-quinoline-3-carboxamide, N-methyl-N-(4-chloro-phenyl)-1,2-dihydro-4-hydroxy-5-methoxy-1-methyl-2-oxo-quinoline-3-carboxamide, N-methyl-N-(4-trifluoromethyl-phenyl)-1,2-dihydro-4-hydroxy-5-methoxy-1-methyl-2-oxo-quinoline-3-carboxamide, N-methyl-N-(2,4-difluoro-phenyl)-1,2-dihydro-4-hydroxy-5,6-methylenedioxy-1-methyl-2-oxo-quinoline-3-carboxamide, N-methyl-N-(4-methoxy-phenyl)-1,2-dihydro-4-hydroxy-5-trifluoromethyl-1-methyl-2-oxo-quinoline-3-carboxamide.

Several spontaneously occurring autoimmune diseases in man have experimental models that are spontaneously occurring in certain strains of laboratory animals or can be induced in laboratory animals by immunization with specific antigen(s) from the target organ.

Experimental autoimmune encephalomyelitis (EAE) as a model for autoimmune inflammatory diseases of the central nervous system (CNS) has been the most widely used model for the human disease multiple sclerosis.

Autoimmunity to type II collagen can experimentally be induced in certain strains of mice or rats and may lead to the development of polyarthritis. The collagen induced arthritis has several features in common with the human disorder rheumatoid arthritis.

The hallmark of asthma in humans is an increased reactivity of the airways to a range of chemical and physical stimuli. It is now widely accepted that products released from inflammatory cells, e.g. activated eosinophils, comprise epithelial integrity and promote bronchial hyperresponsiveness. The murine model of ovalbumin (OA)-induced lung inflammation is dominated by the temporally regulated influx of lymphocytes and eosinophils into the bronchial lumen.

Roquinimex has been found to induce the Beagle Pain Syndrome (BPS)(15,16) in different breeds of beagle dogs. The disease is reflected by clinical and laboratory manifestations justifying BPS as a model for the flu-like syndrome induced by roquinimex in man.

The compounds of general formula (I) were assayed for inhibition of acute experimental autoimmune encephalomyelitis (aEAE) in mice. Roquinimex was used as treatment control and showed a more than 50% inhibition at ≧5 mg/kg. Surprising and unexpected results were obtained when introducing proper substitution in the 5-position of the quinoline ring. In comparison with roquinimex, the potency of the 5-chloro substituted compound was increased a 100-fold. Substitution in the 6-, 7-, and 8-position resulted in less active compounds. The effect of the 5-substitution could largely be understood on physicochemical grounds. In general EAE activity as seen by the EAE inhibition was in the following descending order according to the position of the substitution: 5>6>>7=8. The comparison of the effects of 5- and 6-substitution showed that there is a statistically significant difference on every normal level (p<0.001) between the two, the effect of the 5-substitution being superior. Furthermore, proper aromatic substitution in the quinoline moiety and the 3-carboxamide moiety of the compounds of general formula (I) significantly reduced or even abolished the side effects, i.e. the teratogenic effect and the BPS, of roquinimex. Thus, physicochemical properties of the 5-substituent in the quinoline moiety and the ortho-, meta- and/or, in particular, the para-substituent in the 3-carboxamide moiety are of major importance for an improved risk/benefit ratio in comparison with roquinimex. Replacement of the methyl group on the carboxamide nitrogen with a higher alkyl group reduced the side effects even further. Hence, the compounds of formula (I) have surprisingly been found to be both chemically and pharmacologically different from those drugs hitherto suggested for the treatment of MS and its manifestations.

All embodiments of the invention as disclosed in the claims are herewith included in the specification.

The following examples are intended to illustrate the invention without restricting the scope thereof.

The compounds of general formula (I) may be prepared by methods known in the literature and the following methods:

Method A:

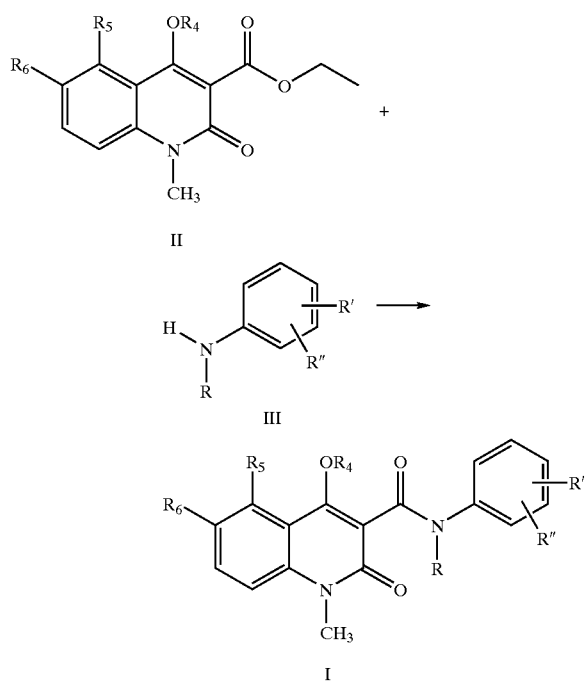

The compounds of general formula (I) may be prepared by known methods and, for example, as shown above, by reaction of an ester derivative of the quinoline carboxylic acid with an aniline in a suitable solvent such as toluene, xylene and the like. General methods for preparation of the quinoline carboxylic acid ester derivatives of formula (II) are described below. N-alkylated anilines of formula (III) are commercially available or known from literature, e.g. in Johnstone et al, J. Chem. Soc. 1969, 2223–2224. Compounds falling within the scope of formula (III) may be prepared by methods, which are generally analogous to those of said literature.

Method B:

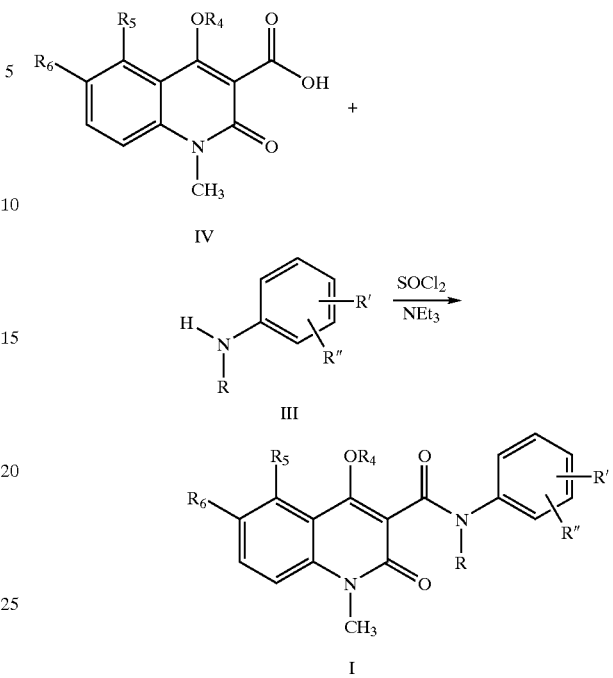

The compounds of formula (I) may also be prepared by reaction of a quinoline carboxylic acid of formula (IV) with an aniline of formula (III). Various coupling reagents known in the art may be used, e.g., carbodiimides known from literature in U.S. Pat. No. 4,547,511. One suitable coupling method utilises thionyl chloride in the presence of triethylamine and a suitable solvent such as dichloromethane. This method may be used in instances when direct coupling between ester and aniline does not work, e.g., when the aniline contains electron withdrawing substituents. The quinoline carboxylic acids of formula (IV) may be obtained from the corresponding esters of formula (II) by acidic hydrolysis as described below.

EXAMPLE 1

1,2-Dihydro-4-hydroxy-5-methoxy-1-methyl-2-oxo-quinoline-3-carboxylic Acid Ester Ethyl Ester To a solution of 2,6-difluorobensonitril (42 g, 0.30 mol) in 150 ml of anhydrous methanol sodium methoxide (17.9 g, 0.33 mol) was slowly added at 30° C. After being heated under reflux for 1 hour, aqueous 40% methylamine (133 ml, 1.2 mol) was added and the resulting solution refluxed for 4 days. On cooling, a white solid, 2-methoxy-6-(methylamino)bensonitrile, precipitated which was collected by filtration. The precipitate was dissolved in an aqueous solution of ethylene glycol (500 ml) and potassium hydroxide (14 g). The solution was refluxed at 150° C. over night, cooled to room temperature and the pH adjusted to 4 with conc. hydrochloric acid. The anthranilic acid formed was collected by filtration, washed with water (50 ml) and dried under vacuum. To the 5-methoxy-N-methyl-anthranilic acid (32 g, 0.18 mol) dissolved in 200 ml of dioxane, phosgene (44 g, 0.45 mol) was slowly added under cooling in an ice bath. The mixture was warmed at 40° C. for 1 hour, and then cooled to 15° C. The isatoic anhydride formed was collected by filtration. After being carefully dried, the 5-methoxy-N-methyl-isatoic anhydride (20.7 g, 0.10 mol) was added to a solution of sodium diethylmalonate (31 g, 0.17 mol) in 250 ml of anhydrous N,N- dimethylformamide at room temperature. The solution was heated at 100° C. for 3 hours, cooled to room temperature, 250 ml of water was added and the pH adjusted to 4 with conc. hydrochloric acid. The precipitate was collected by filtration and dried in vacuum to give the title compound as pure white crystals (22 g), yield 48%.

1H NMR (CDCl$_3$) δ 1.43 (t, 3H), 3.62 (s, 3H), 3.96 (s, 3H), 4.45 (q, 2H), 6.70 (d, 1H), 6.92 (d, 1H), 7.55 (t, 1H), 13.5 (s, 1H).

EXAMPLE 2
1,2-Dihydro-4-hydroxy-5-chloro-1-methyl-2-oxo-quinoline-3-carboxylic Acid Ethyl Ester Phosgene (51 g, 0.52 mol) dissolved in 150 ml of dioxane was added in portions to a mechanically stirred slurry of 2-amino-6-chloro-benzoic acid (30 g, 0.175 mol) and sodium bicarbonate (44 g, 0.52 mol) in 300 ml of dioxane. Violent reaction with gas evolution occurred and the reaction mixture was cooled to keep the temperature below 50° C. Then stirring was continued at 50° C. for 1 hour. The reaction mixture was cooled to 15° C., the resulting precipitate was collected, washed with water and dried to give the isotopic anhydride. The anhydride (5 g, 0.025 mol) was dissolved in 50 ml of N,N-dimethylacetamide and cooled to 0° C. Sodium hydride (75%)(0.94 g, 0.028 mol) and then methyl iodide (1.89 ml, 0,030 mol) was added at a rate to keep the temperature below 5° C. The reaction mixture was stirred at room temperature for 5 hours. The remaining methyl iodide was removed under vacuum. Sodium hydride (0.94 g, 0.028 mol) was added together with diethyl malonate (4.5 g, 0.028 mol). The mixture was heated at 85° C. for 5 hours. After cooling to room temperature, 50 ml of methanol and 50 ml of 1 M hydrochloric acid and subsequently 250 ml of water were added. An emulsion was formed which crystallised on standing in a refrigerator for 72 hours. The crystalline mass was collected by filtration, washed with water, water/methanol (1.1) and heptane and dried to afford the title compound (6.3 g), yield 74%.

1H NMR (CDCl$_3$) δ 1.46 (3H, t), 3.63 (3H, s), 4.49(2H, q), 7.23(1H, d), 7.27 (1H, d), 7.49 (1H, t), 15.0(1H, s).

EXAMPLE 3
1,2-Dihydro-4-hydroxy-5-trifluoromethyl-1-methyl-2-oxo-quinoline-3-carboxylic Acid Ethyl Ester 2-Fluoro-6-(trifluoromethyl)benzonitrile (10 g, 0.053 mol) was warmed at 40° C. in 200 ml of anhydrous methylamine in an autoclave for 2 days. The excess methylamine was allowed to evaporate and the resulting grey solid was dissolved in 200 ml of methylene chloride together with 4-aminopyridine (0.1 g, 0.001 mol) and triethylamine (3.3 ml, 0.026 mol). To the chilled solution was slowly added ethyl malonyl chloride (8.8 g, 0.060 mol). The solution was stirred for 4 hours and then worked up to give a yellowish syrup. The syrup was dissolved in 100 ml of anhydrous ethanol, and sodium methoxide (5.4 g, 0.10 mol) was added. After 1 hour, the solvent was removed and the residue worked up with methylene chloride and water. The quinoline derivative formed was carefully dried and suspended in 250 ml of chilled anhydrous tetrahydrofuran. Sodium hydride (4 g, 0.125 mol) was slowly added and then methyl iodide (10 ml, 0.15 mol). The mixture was heated under reflux for 6 hours, quenched with water and worked up with diethyl ether. The solvents were removed and the residue (17.3 g) was dissolved in a mixture of ethanol (50 ml) and conc. hydrochloric acid (10 ml). The solution was warmed at 45° C. overnight, cooled and the precipitate was collected to give 8 g of the title compound, yield 48%.

1H NMR (CDCl$_3$) δ 1.46 (3H, t), 3.68 (3H, s), 4.50(2H, q), 7.58 (1H, m), 7.71 (2H, m), 15.0 (1H, s).

In essentially the same manner the following compound was obtained from the corresponding starting materials:

1,2-Dihydro-4-hydroxy-5-trifluoromethoxy-1-methyl-2-oxo-quinoline-3-carboxylic acid ethyl ester.

EXAMPLE 4
1,2-dihydro-4-hydroxy-1-methyl-2-oxo-5,6-methylenedioxy-quinoline-3-carboxylic Acid Ethyl Ester Di-tert-butyl dicarbonate (36 g, 0.17 mol) was added portionwise to a solution of 3,4-(methylenedioxy)-aniline (20.6 g, 0.15 mol) in anhydrous tetrahydrofuran (150 ml). The solution was reflux heated for 2 hours, then concentrated under vacuum to give a black solid residue. The residue was dissolved in anhydrous tetrahydrofuran (600 ml) and cooled to −40° C. A hexane solution of 1.3 M sec-butyllithium (265 ml, 0.35 mol) was added dropwise. After stirring the solution for 0.5 hour at −40° C. dry ice (ca 40 g) pellets were added. The mixture was allowed to warm to 0° C. and water (ca 700 ml) was added. The aqueous solution was acidified with hydrochloric acid to a pH 3 and extracted with ether. The extracts were dried and concentrated to give the N-tBoc protected 5,6-methylenedioxy-anthranilic acid as a solid residue (45 g). This acid was added to an ice-cooled suspension of sodium hydride (80% in oil, 9.0 g, 0.30 mol) in N,N-dimethylformamide (200 ml). The mixture was stirred for 0.5 hour and methyl iodide (22 ml, 0.35 mol) was added. The mixture was stirred at room temperature overnight, was quenched with water (600 ml) and extracted tree times with ether. The organic layer was washed with sat. brine, dried and concentrated under vacuum to give a darkbrown oil. The oil was dissolved in methanol (400 ml) and conc. hydrochloric acid (80 ml) was added. The solution was stirred overnight at room temperature, neutralised with 5 M sodium hydroxide and extracted three times with ether. The combined extracts were filtered through a column with SiO$_2$ and the eluate concentrated under vacuum to give the methylated anthranilic ester (20 g). The ester was dissolved in dichloromethane (400 ml) and cooled on an ice-bath. Ethyl malonyl chloride (21 g, 0.14 mol) was added and then, after 30 minutes, triethylamine (22 ml, 0.16 mol). After being stirred for 1 hour at room temperature the cloudy mixture was washed with 0.5 M hydrochloric acid and then bicarbonate. The organic phase was carefully dried and concentrated under vacuum. The residue was then dissolved in dry ethanol (200 ml) and sodium methoxide (17 g, 0.32 mol) was added. The mixture was stirred for 1 hour and water was added (300 ml). The solution was washed with ethyl acetate and then the aqueous solution was acidified with conc. hydrochloric acid. The precipitate was collected by filtration and dried under vacuum to give the title compound as grey crystals (17 g, overall yield 41%).

1H NMR (CDCl$_3$) δ 1.45 (3H, t), 3.58 (3H, s), 4.48(2H, q), 6.17 (2H, s), 6.71 (1H, d), 7,14 (1H, d).

EXAMPLE 5
5-Ethyl Isatoic Anhydride

A mixture of chloral hydrate (59.3 g, 0.36 mol), water (700 ml), and sodium sulphate (85.8 g, 0.60 mol), was heated to 50° C. When 50° C. was reached, sequentially a mixture of 3-ethyl aniline (40.8 g, 0.33 mol), water (700 ml) and conc. hydrochloric acid (33.6 ml) and a mixture of hydroxylamine hydrochloride (74.8 g, 1.04 mol) and water (330 ml) were added. The resulting mixture was heated to 80° C. during 30 minutes and kept another 10 minutes at this temperature before the reaction mixture was cooled on an ice-bath. The resulting precipitate was filtered off, washed with water and dried in vacuum over P$_2$O$_5$ to give an isonitrosoacetanilide (36.6 g), yield 58%. The isonitrosoacetanilide (10.0 g, 0.05 mol), was added portionwise to a mixture of water (9 ml) and conc. sulphuric acid (60 ml) prewarmed to 50° C., maintaining the temperature between 50–55° C. When the addition was completed, the mixture was heated to 80° C. and kept at this temperature for 10 minutes. The reaction mixture was then cooled on an ice-bath and poured on 10–12 times the reaction volume of crushed ice. The mixture was then left standing for about one hour. The water suspension was extracted with dichloromethane which was dried and evaporated resulting in an mixture of the two analogues 4-ethyl and 6-ethyl isatins approximately 0.68:1(7.6 g), yield 84%.

The mixture of the two isomers was dissolved in aqueous sodium hydroxide and the solution was filtered through celite and then acidified to pH 4. The 4-analogue was at this pH extracted into dichloromethane which was dried and evaporated to give the pure 4-ethyl isatin (3.1 g), yield 34%.

4-Ethyl isatin (3.1 g, 0.018 mol) was added to a mixture of conc. sulphuric acid (45 μl) in acetic acid (14 ml). The suspension was warmed to 30° C., hydrogen peroxide 35% (2.2 ml) was added and after the addition the temperature was raised to 65° C. After being heated for 3 hours, the mixture was cooled and the precipitate filtered off, washed with water and dried to give the title compound (1.7 g), yield 48%.

1H NMR (DMSO-d$_6$) δ 1.12(3H, t), 3.02(2H, q), 6.98 (1H, d), 7.05 (1H, d), 7,58 (1H, t), 11.6 (1H, broad).

EXAMPLE 6
1,2-Dihydro-4-hydroxy-5-methoxy-1-methyl-2-oxo-quinoline-3-carboxylic Acid While cooling, 10 ml of conc. hydrochloric acid was added to 30 ml of acetic anhydride. To this solution, 1,2-dihydro-4-hydroxy-5-methoxy-1-methyl-2-oxo-quinoline-3-carboxylic acid ethyl ester (10.5 g, 38 mmol) was added and the mixture heated at 80° C. for 14 hours. The mixture cooled to room temperature and the crystalline product was filtered off, washed with cold methanol and dried to yield the title compound (7.2 g), yield 77%.

1H NMR ((CDCl$_3$) δ 3.73(3H, s) 4.02(3H, s), 6.82(1H, d), 7.02(1H, d), 7.62(1H, t)

EXAMPLE 7
N-Methyl-N-phenyl-1,2-dihydro-4-hydroxy-5-methoxy-1-methyl-2-oxo-quinoline-3-carboxamide (Not Included in the Claims)
(Method A)

N-Methylaniline (2.7 g, 0.025 mol) was dissolved in 80 ml of toluene and about 30 ml of the solvent was distilled off in order to obtain a dry solution. 1,2-Dihydro-4-hydroxy-5-methoxy-1-methyl-2-oxo-quinoline-3-carboxylic acid ethyl ester (2.7 g, 0.01 mol) was added to the boiling solution. The ethanol formed during the reaction was distilled off together with some toluene for about 4 hours. The mixture was cooled to room temperature. The precipitate was collected, washed with cold toluene and hexane and dried to give the title compound (2.8 g), yield 83%.

1H NMR (CDCl$_3$) δ 3.49(3H, s), 3.50(3H, s), 4.03(3H, s), 6.66(1H, d), 6.68 (1H, d), 7.08–7.48(6H, m).

13C NMR (CDCl$_3$) δ 29.7(CH3), 36.8(CH3), 56.8(CH3), 103.3(CH), 104.2(C), 108.4(CH), 110.2(C), 126.2(CH), 127.2(CH), 128.6(CH), 131.4(CH), 141.2(C), 143.6(C), 157.0(C), 157.4(C), 160.3(C), 165.1(C).

ESI MS/MS [M+H]$^+$339, fragment 232.

In essentially the same manner the following compounds were obtained from the corresponding starting materials:

N-methyl-N-phenyl-1,2-dihydro-4-hydroxy-5-chloro-1-methyl-2-oxo-quinoline-3-carboxamide (not included in the claims) 1H NMR (CDCl$_3$) δ 3.38(3H, s), 3.52 (3H, s), 7.08–7.34(7H, m), 7.43(1H, t).

13C NMR (CDCl$_3$) δ 29.9(CH3), 38.5(CH3), 104.7(C), 112.8(C), 113.3(CH), 125.5(CH), 125.6(CH), 126.8 (CH), 128.7(CH), 131.8(CH), 132.9(C), 142.6(C), 143.9(C), 158.0(C), 166.1(C), 169.3(C).

ESI MS/MS [M+H]$^+$343, fragments 236 and 108.

N-ethyl-N-(3-methoxy-phenyl)-1,2-dihydro-4-hydroxy-5-ethyl-1-methyl-2-oxo-quinoline-3-carboxamide, N-methyl-N-(4-chloro-phenyl)-1,2-dihydro-4-hydroxy-5-chloro-1-methyl-2-oxo-quinoline-3-carboxamide, 1H NMR (CDCl$_3$) δ 3.38(3H, s), 3.45(3H, s), 7.12–7.28-(6H, m) 7.45(1H, t)

13C NMR (CDCl$_3$) δ 30.0(CH3), 38.4(CH3), 104.5(C), 112.6(C), 113.4(CH), 125.6(CH), 127.0(CH), 128.9 (CH), 131.9(CH), 132.4(C), 132.8(C), 142.5(C), 142.6(C), 158.0(C), 166.0(C), 169.2(C).

ESI MS/MS [M+H]$^+$377, fragments 236 and 142.

N-ethyl-N-(4-methoxy-phenyl)-1,2-dihydro-4-hydroxy-5-chloro-1-methyl-2-oxo-quinoline-3-carboxamide, 1H NMR (CDCl$_3$) δ 1.18(3H, t), 3.33(3H, s), 3.74(3H, s), 3.90(2H, q, broad), 6.73(2H, d), 7.05–7.15(3H, m), 7.22(1H, d), 7.39(1H, t).

13C NMR (CDCl$_3$) δ 12.4(CH3), 31.1(CH3), 45.6(CH2), 55.4(CH3), 109.5(C), 111.5(C), 114.2(CH), 115,2(CH), 126.2(CH), 127.9(CH), 130.4(C), 132.2(CH), 133.1 (C), 141.7(C), 159.2(C), 159.3(C), 160.1(C), 166.7(C).

ESI MS/MS [M+H]$^+$387, fragments 236 and 152.

N-methyl-N-(4-methoxy-phenyl)-1,2,-dihydro-4-hydroxy-5-chloro-1-methyl-2-oxo-quinoline-3-carboxamide, 1H NMR (CDCl$_3$) δ 3.37(3H, broad signal), 3.43(3H, s), 3.75(3H, s), 6.75(2H, broad signal), 7.14(3H, broad signal), 7.22(1H, d), 7.40(1H, t).

13C NMR (CDCl$_3$) δ 30.0(CH3), 38.5(CH3), 55.4(CH3), 105.4(C), 112.8(C), 113.4(CH), 113.9(CH), 125.5 (CH), 127.0(CH), 131.7(CH), 132.7(C), 136.8(C), 142.6(C), 158.1(C), 158.3(C), 164.9(C), 169.1(C).

ESI MS/MS [M+H]$^+$373, fragments 236 and 138.

N-ethyl-N-(3-fluoro-phenyl)-1,2-dihydro-4-hydroxy-5-chloro-1-methyl-2-oxo-quinoline-3-carboxamide, 1H NMR (CDCl$_3$) δ 1.20(3H, t), 3.33(3H, s), 3.95(2H, q), 6.84–6.98(3H, m), 7.11–7.20(2H, m), 7.23(1H, d), 7.42 (1H, t).

13C NMR (CDCl$_3$) δ 12.9(CH3), 29.9(CH3), 45.8(CH2), 104.7(C), 112.7(C), 113.4(CH), 113.8+114.0(CH), 113.9+114.1(CH), 122.3+122.4(CH), 125.6(CH), 129.5+129.6(CH), 131.9(CH), 132.8(CH), 142.7(C), 143.7+143.8(C), 158.0(C), 161.4+163.4(C), 165.9(C), 168.8(C); some peaks are multiplets due to F-coupling.

ESI MS/MS [M+H]$^+$375, fragments 236 and 140.

N-methyl-N-(2-fluoro-phenyl)-1,2-dihydro-4-hydroxy-5-methoxy-1-methyl-2-oxo-quinoline-3-carboxamide, 1H NMR (CDCl$_3$) δ 3.47(3H, s), 3.53(3H, s), 4.03(3H, s), 6.68(1H, d), 6.88–6.96(2H, m), 7.02–7.07(1H, m),7.12–7.17(1H, m), 7.42–7.49(2H, m).

13C NMR (CDCl$_3$) δ 30.7(CH3), 36.8(CH3), 57.1(CH3), 104.3(CH), 104.4(CH), 107.2(CH), 109.2(C), 116.4+116.6(CH), 124.3+124.3(CH), 128.7(CH), 129.9+130.0(C), 129.9+130.0(CH), 132.9(CH), 141.1(C), 157.4(C), 157.4(C), 156.8+158.8(C), 160.3(C), 167.0 (C).

ESI MS/MS [M+H]$^+$357, fragment 232.

N-methyl-N-(3-chloro-phenyl)-1,2-dihydro-4-hydroxy-5-methoxy-1-methyl-2-oxo-quinoline-3-carboxamide, 1H NMR (CDCl₃) δ 3.40(3H, s), 3.50(3H, s), 4.02(3H, s), 6.67(1H, d, broad), 6.90(1H, d, broad), 7.1(2H, broad), 7.28(1H, broad), 7.38(1H, broad), 7.43(1H, t, broad).

13C NMR (CDCl₃) δ 29.8(CH3), 36.8(CH3), 57.0(CH3), 103.5(CH), 104.3(C), 108.6(CH), 109.9(C), 124.7 (CH), 126.5(CH), 127.5(CH), 129.7 (CH), 131.7(CH), 133.9(C), 141.4(C), 144.8(C), 157.2(C), 157.7(C), 160.3(C), 165.0(C).

ESI MS/MS [M+H]⁻373, fragment 232.

N-ethyl-N-(3-fluoro-phenyl)-1,2-dihydro-4-hydroxy-5-methoxy-1-methyl-2-oxo-quinoline-3-carboxamide, 1H NMR (CDCl₃) δ 1.22(3H, t), 3.50(3H, s), 3.92(2H, broad signal), 4.02(3H, s), 6.66(1H, d), 6.81–6.92(2H, m), 7.08–7.19(3H, m), 7.41(1H, t).

13C NMR (CDCl₃) δ 13.1(CH3), 29.8(CH3), 43.9(CH2), 56.9(CH3), 103.4(CH), 104.3(c), 108.6(CH), 110.4(C), 114.5+114.7(CH), 123.4(CH), 129.6+129.7(CH), 131.6(CH), 141.4(C), 143.5(C), 157.2(C), 157.4(C), 160.3(C), 161.4+163.3(C), 164.4(C); some peaks are multiplets due to F-coupling.

ESI MS/MS [M+H]⁺371, fragment 232.

N-methyl-N-(4-chloro-phenyl)-1,2-dihydro-4-hydroxy-5-methoxy-1-methyl-2-oxo-quinoline-3-carboxamide, 1H NMR (CDCl₃) δ 3.46(3H, s), 3.52(3H, s), 4.05(3H, s), 6.69(1H, d), 6.92(1H, d), 7.10–7.38(4H, dd), 7.45(1H, t).

13C NMR (CDCl₃) δ 29.8(CH3), 36.8(CH3), 56.8(CH3), 103.4(CH), 104.2(C), 108.6(CH), 110.0(C), 127.6 (CH), 128.9(CH), 131.6(CH), 132.8(C), 141.3(C), 142.2(C), 157.1(C), 157.5(C), 160.3(C), 165,0(C).

ESI MS/MS [M+H]⁺373, fragment 232.

N-ethyl-N-(2-fluoro-phenyl)-1,2-dihydro-4-hydroxy-5-trifluoromethyl-2-oxo-quinoline-3-carboxamide N-methyl-N-(4-chloro-phenyl)-1,2-dihydro-4-hydroxy-5-trifluoromethyl-1-methyl-2-oxo-quinoline-3-carboxamide, 1H NMR (CDCl₃) δ 3.40(3H, s), 3.48(3H, s), 7.08–7.25 (4H, m), 7.48(1H, d), 7.65(1H, t), 7.69(1H, t).

13C NMR (CDCl₃) δ 30.1(CH3), 38.7(CH3), 103.8(C), 112.7(C), 113.4(C), 118.7(CH), 121.9+121.9+122.0+122.0(CH), 120.3+122.4+124.6+126.8(C), 127.0(CH), 127.8+128.0+128.3+128.5(C), 128.9(CH), 131.6(CH), 132.4(C), 142.3(C), 142.6(C), 157.7(C), 166.3(C), 169.9(C); some peaks are multiplets due to F-coupling.

ESI MS/MS [M+H]⁺411, fragments 270 and 142.

N-methyl-N-(4-methoxy-phenyl)-1,2-dihydro-4-hydroxy-5-trifluoromethyl-1-methyl-2-oxo-quinoline-3-carboxamide, N-methyl-N-(4-chloro-phenyl)-1,2-dihydro-4-hydroxy-5-trifluoromethoxy-1-methyl-2-oxo-quinoline-3-carboxamide, N-methyl-N-(4-methoxy-phenyl)-1,2-dihydro-4-hydroxy-5-trifluoromethoxy-1-methyl-2-oxo-quinoline-3-carboxamide, N-methyl-N-phenyl-1,2-dihydro-4-hydroxy-5-chloro-6-methoxy-1-methyl-2-oxo-quinoline-3-carboxamide, (not included in the claims)

1H NMR (CDCl₃) δ 3.38(3H, s, broad), 3.52(3H, s), 3.96(3H, s), 7.14–7.23(2H, m), 7.23–7.30(5H, m).

13C NMR (CDCl₃) δ 29.7(CH3), 38.3(CH3), 57.2(CH3), 113.6(CH), 113.7(C), 116.8(CH), 120.3(C), 125.8 (CH), 126.9(CH), 128.7(CH), 136.5(C), 143.9(C), 150.9(C), 158.0(C), 165 (C), 168.9(C).

ESI MS/MS [M+H]⁺373, fragments 266 and 108.

N-methyl-N-(4-chloro-phenyl)-1,2-dihydro-4-hydroxy-5,6-methylenedioxy-1-methyl-2-oxo-quinoline-3-carboxamide.

EXAMPLE 8
N-Methyl-N-(4-trifluoromethyl-phenyl)-1,2-dihydro-4-hydroxy-5-methoxy-1-methyl-2-oxo-quinoline-3-carboxamide(Method B)

To an ice-cold solution of 1,2-dihydro-4-hydroxy-5-methoxy-1-methyl-2-oxo-quinoline-3-carboxylic acid(8 g, 0.032 mol), triethylamine (15.5 ml, 0.11 mol) and 4-trifluoromethyl-N-methylaniline(6.1, 0.035 mol) in 150 ml of methylene chloride was added dropwise during 0.5 hours a solution of thionyl chloride (3.0 ml, 0.042 mol) in 10 ml of methylene chloride. The stirring was continued at 4° C. for 4 hours. The solution was diluted with 10 ml of methylene chloride, washed with cold 1 M sulphuric acid and then extracted with 1 M sodium hydroxide. The pH of the aqueous phase was adjusted to 8–8.5, clarified by filtration and then acidified with hydrochloric acid to pH 4. On standing a crystalline precipitate was formed which was filtered off, washed with water and dried to give the title compound (8.5 g) yield 65%.

1H NMR (CDCl₃) δ 3.48(3H, s), 3.54(3H, s), 4,06(3H, s), 6.70(1H, d), 6.94(1H, d), 7.46(1H, t), 7.50(4H, broad signal).

13C NMR (CDCl₃) δ 29.8(CH3), 36.9(CH3), 56.9(CH3), 103.5(CH), 104.2(C), 108.7(CH), 109.5(C), 117.3+121.7+126.0+130.3(C), 125.8+125.9+125.9+126.0(CH), 126.3 (CH), 127.9+128.4+128.9+129.4(C), 131.8(CH), 141.4(C), 146.7(C), 157.2(C), 158.0(C), 160.3(C), 165,0(C); some peaks are multiplets due to F-coupling.

ESI MS/MS [M+H]⁺407, fragment 232.

In essentially the same manner the following compounds were obtained from the corresponding starting materials:

N-ethyl-N-(4-trifluoromethyl-phenyl)-1,2-dihydro-4-hydroxy-5-chloro-1-methyl-2-oxo-quinoline-3-carboxamide, 1H NMR (CDCl₃) δ 1.22(3H, t), 3.28(3H, s), 3.99(2H, q), 7.13(1H, d), 7.23–7.32(3H, m), 7.40–7.51(3H, m).

13C NMR (CDCl₃) δ 13.0(CH3), 29.8(CH3), 45.8(CH2), 104.0(C), 112.7(C), 113.5(CH), 120.6+122.8+124.9+127.1(C), 125.7(CH), 125.7+125.7+125.8+125.8(CH), 126.7(CH), 128.3+128.6+128.8+129.1(C), 132.1(CH), 133.0(C), 142.8(C), 145.6(C), 157.9(C), 166.8(C), 169, 1(C); some peaks are multiplets due to F-coupling.

ESI MS/MS [M+H]⁺425, fragments 236 and 190.

N-ethyl-N-(4-trifluoromethyl-phenyl)-1,2-dihydro-4-hydroxy-5-methoxy-1-methyl-2-oxo-quinoline-3-carboxamide, 1H NMR (CDCl₃) δ 1.22(3H, t), 3.51(3H, s), 3.93(2H, q), 4.02(3H, s), 6.67(1H, d), 6.91(1H, d), 7.43(1H, t), 7.46–7.52(4H, m).

13C NMR (CDCl₃) δ 13.2(CH3), 29.8(CH3), 44.1(CH2), 56.9(CH3), 103.5(CH), 104.3(C), 108.7(CH), 110.0 (C), 120.7+122.9+125.0+127.2(C), 125.9+125,9(CH), 127.7(CH), 128.9+129.2+129.4+129.7(C), 131.8(CH), 141.5(C), 145.3(C), 157.2(C), 157.8(C), 160.3(C), 164.4(C); some peaks are multiplets due to F-coupling.

ESI MS/MS [M+H]⁺421, fragments 232 and 206.

N-methyl-N-(4-trifluoromethoxy-phenyl)-1,2-dihydro-4-hydroxy-5-methoxy-1-methyl-2-oxo-quinoline-3-carboxamide, N-methyl-N-(2,4-difluoro-phenyl)-1,2-dihydro-4-hydroxy-5-chloro-1-methyl-2-oxo-quinoline-3-carboxamide, 1H NMR (CDCl₃) δ 3.33(3H, s), 3.45(3H, s), 6.62(1H, broad), 6.83(1H, broad), 6.98–7.17(2H, m, broad), 7.20 (1H, d), 7.37(1H, t, broad).

13C NMR (CDCl₃) δ 29.9(CH3), 37.3(CH3), 103.3(C), 104.7+104.9+105.1(CH), 110.5+110.7(CH), 112.7(C), 113.3(CH), 125.7(CH), 128.1(C), 128.6(CH), 132.1 (CH), 133.3(C), 142.8(C), 157.8(C), 156.9+157.0+ 158.9+159.0(C), 160.6+160.6(C), 167.4(C), 170.4(C); some peaks are multiplets due to F-coupling.

ESI MS/MS [M+H]⁺379, fragments 236 and 144.

N-methyl-N-(2,5-difluoro-phenyl)-1,2-dihydro-4-hydroxy-5-chloro-1-methyl-2-oxo-quinoline-3-carboxamide, N-methyl-N-(2,4-difluoro-phenyl)-1,2-dihydro-4-hydroxy-5-methoxy-1-methyl-2-oxo-quinoline-3-carboxamide, 1H NMR (CDCl₃) δ 3.40(3H, s), 3.51(3H, s), 4.02(3H, s), 6.60–6.63(1H, m), 6.63(1H, d), 6.73–6.79(1H, m), 6.90 (1H, d), 7.38–7.46(2H, m).

13C NMR (CDCl₃) δ 29.9(CH3), 36.0(CH3), 56.9(CH3), 103.5(CH), 104.2(C), 104.4+104.6+104.6+104.8(CH), 108.6(CH), 109.2(C), 110.8+110.9+111.0+111.0(CH), 127.3+127.3+127.4+127.4(C), 130.0+130.1(CH), 131.8(CH), 141.4(C), 157.2(C), 157.3+157.4+159.3+ 159.4(C), 158.5(C), 160.3(C), 160.7+160.8+162.6+ 162.7(C), 165.5(C); some peaks are multiplets due to F-coupling.

ESI MS/MS [M+H]⁺375, fragment 232.

N-methyl-N-(2,5-difluoro-phenyl)-1,2-dihydro-4-hydroxy-5-methoxy-1-methyl-2-oxo-quinoline-3-carboxamide, 1H NMR (CDCl₃) δ 3.48(3H, s), 3.64(3H, s), 4,10(3H, s), 6.60–7.30(5H, m), 7.63(1H, t).

13C NMR (CDCl₃) δ 31.0(CH3), 37.2(CH3), 57.2(CH3), 104.4(C), 105.0(CH), 105.7(C), 109.5(C), 115.2+115.6 (CH), 116.8+116.9(CH), 117.2+117.3+117.5+117.7 (CH), 129.8+130.0+130.0+130.2(C), 133.9(C), 141.0 (C), 151.9+155.8(C), 157.6(C), 155.8+159.6(C), 161.4 (C), 161.7(C), 167,6(C); some peaks are multiplets due to F-coupling.

ESI MS/MS [M+H]⁺375, fragment 232.

N-methyl-N-(2,4-difluoro-phenyl)-1,2-dihydro-4-hydroxy-5,6-methylenedioxy-1-methyl-2-oxo-quinoline-3-carboxamide.

Pharmacological Methods

Acute Experimental Autoimmune Encephalomyelitis (aEAE)

SJL/N female mice, 8 weeks of age, were used for the experiments. Mouse spinal cord homogenate (MSCH) was obtained from 8 to 12 weeks-old C57B1/6 female mice. The tissue was homogenised on ice and diluted ion cold PBS. Incomplete Freunds' containing 1 mg/ml M. tuberculosis hominis H37Ra was emulsified with an equal volume of MSCH to give a final concentration of 10 mg/ml of MSCH. The inoculum volume of 0.1 ml was injected intradermally at the base of the tail. Pertussis toxin was injected i.p. at day 0 and 3 after immunization. Treatment was given per os daily either at day 3 to 12 post-immunization or days 3 to 7 and 10 to 12. Control animals received saline. The animals, eight per dose group, were scored for clinical signs of paralytic disease on a scale from 0 to 5 in the following way: 0, normal; 1, limp tail; 2, hind limb paresis; 3, hind limb paralysis and limp foreleg; 4, bilateral hind and fore limb paralysis; 5, death. Clinical scores were monitored at day 7 and daily from day 9 until end of the experiment at day 14. Treatment effects were calculated as percent inhibition of clinical scores compared to saline treated controls.

Collagen Induced Arthritis

DBA/1 male mice between 8 to 10 weeks of age were used for the experiments. On day 0 the mice were immunized intradermally at the base of the tail with bovine type II collagen (100 μg/mouse) in Freund's complete adjuvant. The treatment was given per os daily on days 3 to 7, 10 to 14, 17 to 21, 24 to 28 and 31 to 35. Fifteen days after immunization mice were inspected for signs of arthritis. The animals were inspected three times a week. Every second or third day individual paws of the arthritic animals were scored by a scale from 0–4 (0=no arthritis, 1=arthritis in one of the interpha-lageal, metatarophalangeal or intercarpal joints, 2=two arthritic joints, 3=three arthritic joints, 4=as in 3 but with more severe redness and swelling of the paw). The score of each paw was added to give a maximal attainable score of 16 for each mouse.

Ovalbumin-Induced Lung Inflammation

C57B1/6 female mice between 10 to 14 weeks of age were used for the experiments, 10 mice/group. The mice were sensitised with ovalbumin (OA) in aluminium hydroxide in a volume of 0.2 ml inoculated ip. Treatment was given at day 1 to day 16. Control mice received saline. Fourteen days after the OA sensitisation mice were exposed for 20 minutes to an aerosol of 1.5% w/v of OA in saline produced by a nebulizer. Vehicle-challenged control mice were exposed to saline. Seventy-two hours after OA/vehicle challenge, mice were anaesthetised and bronchoalveolar lavage was preformed by instilling 0.5 ml ice-cold phosphate buffered saline (PBS) into the lungs twice. Total cells counts were determined and differential counts were made based on identification of eosinophils, monocytes/alveolar macrophages, lymphocytes and neutrophils. Eosinophils infiltration into the lung tissue was evaluated by histochemical methods on frozen lung sections using diaminobenzidine tetrahydrochloride (DAB).

Teratogenic Effects in the Rat

The compounds were administered subcutaneously to female rats during pregnancy, i.e. day 8 to 14 of pregnancy. The rats were caesarean sectioned and necropsied on day 20 after fertilisation. The foetuses were examined for external and internal abnormalities.

Beagle Pain Syndrome (BPS)

The compounds were administered intravenously to beagle dogs. The dosage was given for five consecutive days. The dogs were evaluated for clinical and laboratory signs of the pain syndrome, e.g. fever, increased erythrocyte sedimentation rate (ESR), alkaline phosphate (AP), induction of acute phase proteins and vasculitis.

Among preferred compounds are N-methyl-N-(4-trifluoromethyl-phenyl)-1,2-dihydro-4-hydroxy-5-methoxy-1-methyl-2-oxo-quinoline-3-carboxamide and N-methyl-N-(2,4-difluoro-phenyl)-1,2-dihydro-4-hydroxy-5-chloro-1-methyl-2-oxo-quinoline-3-carboxamide hereinafter called Compound A and B, respectively. N-Methyl-N-phenyl-1,2-dihydro-4-hydroxy-5-chloro-1-methyl-2-oxo-quinoline-3-carboxamide and roquinimex are included as reference compounds hereinafter called Compound C and D, respectively:

aEAE inhibition

| | % aEAE Inhibition | | | |
|---|---|---|---|---|
| Dose, mg/kg p.o. | Compound A (invention) | Compound B (invention) | Compound C | Compound D |
| 0.2 | 66 | 59 | 92 | 35 |
| 1 | 86 | 96 | 100 | 40 |
| 5 | 99 | 100 | | 69 |

Teratogenicity in the rat

| | % malformed fetuses | | | |
|---|---|---|---|---|
| Dose, mg/kg p.o. | Compound A (invention) | Compound B (invention) | Compound C | Compound D |
| 6 | 4 | 0 | 37 | not tested |
| 10 | not tested | not tested | not tested | 9 |
| 30 | 2 | | | 30 |

Effective quantities of the compounds of formula (I) are preferably administered to a patient in need of such treatment according to usual routes of administration and formulated in usual pharmaceutical compositions comprising an effective amount of the active ingredient and a suitable pharmaceutically acceptable carrier. Such compositions may take a variety of forms, e.g. solutions, suspensions, emulsions, tablets, capsules, and powders prepared for oral administration, aerosols for inhalations, sterile solutions for parental administration, suppositories for rectal administration or suitable topical formulations. Conventional procedures for the selection and preparation of suitable pharmaceutical formulations are described, for example, in "Pharmaceuticals—The Science of Dosage Form Design", M. B. Aulton, Churchill Livingstone, 1988.

A suitable daily dosage for use in the treatment of MS is contemplated to vary between 0.0005 mg/kg to about 10 mg/kg body weight, in particular between 0.005 mg/kg to 1 mg/kg body weight, depending upon the specific condition to be treated, the age and weight of the specific patient, and the specific patient's response to the medication. The exact individual dosage, as well as the daily dosage, will be determined according to standard medical principles under the direction of a physician.

Various additives to enhance the stability or ease of administration of the drug are contemplated. The pharmaceutical composition may also contain additional therapeutically useful substances other than a compound of formula (I).

REFERENCES

1. Talal, N.: Autoimmune diseases, In: Roitt, I. M and Delves, P. J. (eds.) Encyclopedia of Immunology, pp. 195–198. Academic Press, 1992.
2. Prineas, J. E.: The neuropathology of multiple sclerosis. In: Koetsier, J. C. (ed.) Handbook of Clinical Neurology, pp. 213–257. Elsevier Science Publ., Amsterdam, 1985.
3. Tarkowski, A. Gummarsson, K., Nilsson. L-Å., Lindholm, L. and Stålhandske, T. Successful treatment of autoimmunity in MRL/1 mice with LS2616, a new immunomodulator. Arthritis Rheum. 29(11):1405–1409, 1986.
4. Larsson, E.-L., Joki, A.-L. and Stålhandske, T. Mechanism of action of the new immunomodulator LS2616 on T-cell responses. Int J Immunopharmacol 9(4):425–31, 1987.
5. Wanders, A., Larsson, E., Gerdin, B. and Tufveson G. Abolition of the effect of cyclosporine on rat cardiac allograft rejection by the new immunomodulator LS-2616 (Linomide). Transplantation 47(2): 216–217, 1989.
6. Kalland, T. Regulation of natural killer progenitors: studies with a novel immunomodulator with distinct effects at the precursor level. J Immunol 144(11): 4472–4476, 1990.
7. Gonzalo, J. A., González-García, A. Kalland, T. Hedlund, G., Martinez, C. and Kroemer, G. Linomide, a novel immunomodulator that prevents death in four models of septic shock. Eur J Immunol 23:2372–2374, 1993.
8. Karussis, D. M., Lehmann, D., Slavin, S. et al Treatment of chronic-relapsing experimental autoimmune encephalomyelitis with the synthetic immunomodulator Linomide (quinoline-3-carboxamide). Proc Natl Acad Sci USA 90: 6400–6404, 1993.
9. Gonzalo, J. A., González-García, A. Kalland, T. et al. Linomide inhibits programmed cell death of peripheral T cells in vivo. Eur J Immunol. 24: 48–52, 1994.
10. Gross, D. J., Sidi, H., Weiss, L., Kalland, T., Rosenmann, E. and Salvin, S. Prevention of diabetes mellitus in non-obese diabetic mice by Linomide, a novel immunomodulating drug. Diabetologia 37: 1195–1201, 1994.
11. Karussis, D. M., Lehmann, D., Brenner, T. et al Immunomodulating of experimental autoimmune myasthenia gravis with Linomide. J Neuroimmunol 55(2): 187–193, 1994.
12. Bai, X. F., Shi, F. D., Zhu, J, Xiao, B. G., Hedlund, G. and Link, H. Linomide-induced suppression of experimental autoimmune neuritis is associated with down-regulated macrophage functions. J. Neuroimmunol 76:177–184, 1997.
13. Karussis, D. M., Lehmann, D. et al Treatment of secondary progressive multiple sclerosis with the immunomodulator Linomide. Neurology 47: 341–356, 1996.
14. Andersen, 0., Lycke, J., Tollesson, P. O. et al Linomide reduces the rate of active lesions in relapsing-remitting multiple sclerosis. Neurology 47: 895–900, 1996.
15. Kelly, D. F., Grimsell, C. S. G. and Kenyon, C. J. Polyarthritis in the dog: A case report. Vet Record 92:363–366, 1973.
16. Harcourt, R. A. Polyarthritis in a colony of beagles. Vet Record 102:519–522, 1978.

What is claimed is:

1. N-ethyl-N-(4-trifluoromethyl-phenyl)-1,2-dihydro-4-hydroxy-5-methoxy-1-methyl-2-oxo-quinoline-3-carboxamide, a pharmaceutically acceptable salt or tautomer thereof.

2. A pharmaceutical composition comprising as active ingredient a pharmaceutically effective amount of the compound of claim 1, together with a pharmaceutically acceptable carrier, said pharmaceutical composition being in a unit dosage amount for administration at a daily dose of said compound of 0.0005 mg/kg to about 10 mg/kg body weight.

3. A method of treating a mammal suffering from pathologic inflammation or a disease resulting from autoimmunity comprising administering to said mammal a pharmaceutically effective amount of the compound of claim 1.

4. The method according to claim 3 wherein said mammal is one suffering from multiple sclerosis (MS).

5. The method according to claim 3 wherein said mammal is one suffering from insulin-dependent diabetes mellitus (IDDM).

6. The method according to claim 3 wherein said mammal is one suffering from systemic lupus erythematosus (SLE).

7. The method according to claim 3 wherein said mammal is one suffering from rheumatoid arthritis (RA).

8. The method according to claim 3 wherein said mammal is one suffering from inflammatory bowel disease (IBD).

9. The method according to claim 3 wherein said mammal is one suffering from psoriasis.

10. The method according to claim 3 wherein said mammal is one suffering from an inflammatory respiratory disorder.

11. The method according to claim 3 wherein said mammal is one suffering from atherosclerosis.

12. The method according to claim 3 wherein said mammal is one suffering from stroke.

13. The method according to claim 3 wherein said mammal is one suffering from Alzheimer's disease.

14. The method of claim 3 wherein said effective amount in a daily dose is 0.0005 mg/kg to about 10 mg/kg body weight.

15. The method of claim 3 wherein said effective amount in a daily dose is 0.005 to 1 mg/kg body weight.

* * * * *

UNITED STATES PATENT AND TRADEMARK OFFICE
CERTIFICATE OF CORRECTION

PATENT NO.   : 6,593,343 B2
DATED        : July 15, 2003
INVENTOR(S)  : Bjork et al.

It is certified that error appears in the above-identified patent and that said Letters Patent is hereby corrected as shown below:

Column 1,
Line 32, delete "$R_A$" and insert therefor -- RA --;

Column 2,
Line 45, delete "RAS (O) $_n$" and insert therefor -- $R_A$S (O) $_n$ --;

Column 3,
Line 56, delete "Metal-" and insert therefor -- meta' --;

Column 6,
Line 45, delete "Acid Ester Ethyl Ester" and insert therefor -- Acid Ethyl Ester --;
Line 55, delete "150ºC." and insert therefor -- 150ºC --;
Line 66, delete "Diethylmalonate" and insert therefor -- diethyl malonate --;

Column 7,
Line 21, delete "Isotopic" and insert therefor -- Isatoic --;
Line 23, delete "(75%) (0.94" and insert therfor -- (75%)  (0.94 --;
Line 24, delete "0,030" and insert therefor -- 0.030 --;

Column 8,
Line 7, delete "1,2-dihydro" and insert therefor -- 1,2-Dihydro --;

Column 12,
Line 10, delete "acid(8g" and insert therefor -- acid (8g) --;
Line 12, delete "-N-methylaniline(6.1" and insert therefor -- -N-methylaniline (6.1 --;
Line 60, delete "fragments 232 and 206" and insert therefor -- fragment 232 --;

Column 13,
Line 51, delete "ion cold" and insert therefor -- In cold --;

UNITED STATES PATENT AND TRADEMARK OFFICE
CERTIFICATE OF CORRECTION

PATENT NO. : 6,593,343 B2
DATED : July 15, 2003
INVENTOR(S) : Bjork et al.

It is certified that error appears in the above-identified patent and that said Letters Patent is hereby corrected as shown below:

<u>Column 14,</u>
Line 13, delete "interpha-lagcal, metatarophalangeal" and insert therefor
-- interphalangeal, metatarsophalangeal --.

Signed and Sealed this

Seventh Day of October, 2003

JAMES E. ROGAN
*Director of the United States Patent and Trademark Office*